(12) United States Patent
Higuchi et al.

(10) Patent No.: US 10,634,893 B2
(45) Date of Patent: Apr. 28, 2020

(54) MEDICAL OBSERVATION APPARATUS AND MEDICAL OBSERVATION SYSTEM

(71) Applicant: SONY OLYMPUS MEDICAL SOLUTIONS INC., Tokyo (JP)

(72) Inventors: Gakuji Higuchi, Tokyo (JP); Tomonori Ishikawa, Tokyo (JP); Masataka Kado, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 54 days.

(21) Appl. No.: 15/308,380

(22) PCT Filed: May 25, 2015

(86) PCT No.: PCT/JP2015/064902
§ 371 (c)(1),
(2) Date: Nov. 2, 2016

(87) PCT Pub. No.: WO2015/194319
PCT Pub. Date: Dec. 23, 2015

(65) Prior Publication Data
US 2017/0052358 A1   Feb. 23, 2017

(30) Foreign Application Priority Data

Jun. 20, 2014   (JP) ................. 2014-127686

(51) Int. Cl.
| | | |
|---|---|---|
| B25J 13/00 | (2006.01) | |
| G02B 21/02 | (2006.01) | |
| G02B 21/24 | (2006.01) | |
| G02B 7/00 | (2006.01) | |
| A61B 90/25 | (2016.01) | |

(Continued)

(52) U.S. Cl.
CPC ............ *G02B 21/025* (2013.01); *A61B 90/25* (2016.02); *A61B 90/361* (2016.02); *G02B 7/001* (2013.01);
(Continued)

(58) Field of Classification Search
CPC .... G02B 21/24; G02B 21/245; G02B 21/362; G02B 21/365; G02B 21/025; H04N 7/185; A61B 90/00; A61B 90/25; A61B 90/361
See application file for complete search history.

(56) References Cited

U.S. PATENT DOCUMENTS

| | | | | |
|---|---|---|---|---|
| 5,122,904 A | * | 6/1992 | Fujiwara | ................ A61B 90/25 |
| | | | | 359/510 |
| 6,569,084 B1 | * | 5/2003 | Mizuno | .............. A61B 1/00149 |
| | | | | 248/325 |

(Continued)

FOREIGN PATENT DOCUMENTS

| | | |
|---|---|---|
| JP | 2000-279368 A | 10/2000 |
| JP | 3081580 U | 11/2001 |

(Continued)

OTHER PUBLICATIONS

International Search Report dated Aug. 18, 2015 in PCT/JP2015/064902 filed May 25, 2015.

(Continued)

*Primary Examiner* — Jamie J Atala
*Assistant Examiner* — Patrick E Demosky
(74) *Attorney, Agent, or Firm* — Xsensus LLP

(57) ABSTRACT

[Object] To provide a medical observation apparatus and a medical observation system that can ensure the user's visual field and have good manipulability.
[Solution] A medical observation apparatus includes: a cylindrical unit; an imaging unit provided in a hollow portion of the cylindrical unit and including an optical system configured to collect light from an object to be observed and form an image, and an imaging element configured to photoelectrically convert light collected by the optical system and output an imaging signal; a support unit including at least one set composed of two arm units and a (Continued)

joint unit linking one of the two arm units to the other in a rotationally movable manner and supporting, at its tip portion, the cylindrical unit and the imaging unit in a rotationally movable manner around an axis in a height direction of the cylindrical unit; and an arm manipulation unit provided on a side surface of the cylindrical unit corresponding to an upper side of an image based on the imaging signal and configured to accept a manipulation input that permits a rotational movement of the arm unit.

19 Claims, 8 Drawing Sheets

(51) Int. Cl.
  | | |
  |---|---|
  | *A61B 90/00* | (2016.01) |
  | *G02B 21/36* | (2006.01) |
  | *H04N 7/18* | (2006.01) |
  | *A61B 5/00* | (2006.01) |
  | *A61B 17/00* | (2006.01) |
  | *G02B 21/00* | (2006.01) |
  | *A61B 90/50* | (2016.01) |

(52) U.S. Cl.
  CPC ......... *G02B 21/241* (2013.01); *G02B 21/245* (2013.01); *G02B 21/362* (2013.01); *G02B 21/365* (2013.01); *H04N 7/185* (2013.01); *A61B 2017/0042* (2013.01); *A61B 2090/508* (2016.02); *G02B 21/0012* (2013.01)

(56) References Cited

U.S. PATENT DOCUMENTS

| | | | | |
|---|---|---|---|---|
| 6,837,883 | B2* | 1/2005 | Moll | ............. A61B 19/2203 606/1 |
| 2001/0055062 | A1 | 12/2001 | Shioda et al. | |
| 2004/0246469 | A1 | 12/2004 | Hirose | |
| 2004/0267089 | A1 | 12/2004 | Otsuka et al. | |
| 2005/0020876 | A1 | 1/2005 | Shioda et al. | |
| 2006/0023324 | A1* | 2/2006 | Otsuka | ................. F16M 11/10 359/871 |
| 2008/0058989 | A1* | 3/2008 | Oleynikov | ......... A61B 1/00149 700/259 |

FOREIGN PATENT DOCUMENTS

| | | | | |
|---|---|---|---|---|
| JP | 2003-126115 | A | | 5/2003 |
| JP | 2005-645 | A | | 1/2005 |
| JP | 2005-7189 | A | | 1/2005 |
| JP | 2005-13715 | A | | 1/2005 |
| JP | 2005000645 | A | * | 1/2005 ......... A61B 1/00149 |
| JP | 2005-43458 | A | | 2/2005 |
| JP | 2005043458 | A | * | 2/2005 |
| JP | 2006-14825 | A | | 1/2006 |
| JP | 2006-305156 | A | | 11/2006 |
| JP | 2006305156 | A | * | 11/2006 |
| JP | 2007-236550 | A | | 9/2007 |
| JP | 2006-305156 | A | | 11/2009 |
| JP | 2010206495 | A | * | 9/2010 |
| JP | 2011-104275 | A | | 6/2011 |
| JP | 2014-76204 | A | | 5/2014 |
| WO | WO2014139023 | A1 | * | 1/2000 |
| WO | WO-2014139023 | A1 | * | 9/2014 ......... A61B 17/3421 |

OTHER PUBLICATIONS

Extended European Search Report dated Nov. 29, 2017 in corresponding European Patent Application No. 15809666.9 citing documents AA, AB, AC, AO and AP therein, 8 pages.

Office Action dated Aug. 20, 2018 in Chinese Patent Application No. 201580031608.3, (With English Translation) p. 1-17.

* cited by examiner

MEDICAL OBSERVATION APPARATUS AND MEDICAL OBSERVATION SYSTEM

TECHNICAL FIELD

The present invention relates to a medical observation apparatus and a medical observation system for observing a minute part of an object to be observed.

BACKGROUND ART

Thus far, as a technology for, when performing an operation of a minute part of the brain, the heart, etc. of a patient that is an object to be observed, observing the minute part, a technology that images the minute part and displays the captured image on a monitor has been known (e.g. see Patent Literatures 1 and 2).

For example, in Patent Literature 1, an observation system including an endoscope that is inserted into the surgical site of the patient and a movement mechanism that includes a plurality of arms and a plurality of electromagnetic brakes or the like that regulate the rotational movements of the arms and moves the endoscope is disclosed. In this technology, two switches that release part of the plurality of electromagnetic brakes to set the endoscope to a movable state are provided. The user (operator) manipulates the two switches as appropriate to move the endoscope to a desired position.

In Patent Literature 2, a medical observation apparatus including a lens unit including an imaging unit and a support means that includes, like in the movement mechanism mentioned above, a plurality of arms and a plurality of electromagnetic brakes or the like and supports the lens unit is disclosed. In this technology, the user manipulates a switch for releasing the electromagnetic brakes provided on the upper surface of the lens unit, and thereby moves the lens unit to a desired position.

CITATION LIST

Patent Literature

Patent Literature 1: JP 2005-13715A
Patent Literature 2: JP 2006-14825A

SUMMARY OF INVENTION

Technical Problem

However, in Patent Literature 1 described above, when the user alters the direction of observation of the endoscope, it is highly conceivable that, in a state of grasping the endoscope, the user manipulates the switch provided at the endoscope with the thumb. However, since there is a parallel link mechanism near the switch, it is hard to say that the configuration is easy to grasp. Furthermore, when the endoscope is tilted to tilt the observation field to the side far from or near to the user, the wrist of the user bends gradually to lead to an unnatural posture, and it is very difficult to perform the ON/OFF manipulation of the switch with the thumb while grasping the endoscope.

On the other hand, in Patent Literature 2 described above, the switch for releasing the electromagnetic brake is provided on the upper surface of the lens unit; when the user moves the lens unit, it is conceivable that the user manipulates the switch with the thumb while grasping the lens unit; however, since there is a ball joint mechanism on the back side of the switch, it is hard to say that the configuration is easy to grasp. It is also conceivable that the user continues pushing the switch while holding the lens unit from the upper side with the entire palm of the hand; in this case, the manipulation of repeating the ON/OFF of the switch is a task of extreme difficulty.

Thus, it has been hard to say that the technologies described in Patent Literatures 1 and 2 have good manipulability. To improve the problem, the idea of providing a manipulation grip separately is easily conceived. However, in this case, the lens unit (the endoscope unit) is increased in size, and consequently the visual field is obstructed when the user views the monitor or the surgical site. Furthermore, the mass of the lens unit (the endoscope unit) is increased, and accordingly the size of the movement mechanism is increased; consequently, pressure is put on the space of the operating room. Thus, it has been desired to further reduce the size of the imaging unit or the movement mechanism of the imaging unit.

The present invention has been made in view of the above, and an object of the present invention is to provide a medical observation apparatus and a medical observation system that can ensure the user's visual field and have good manipulability.

Solution to Problem

In order to solve the above problem and achieve the object, a medical observation apparatus according to the present invention includes: a cylindrical unit; an imaging unit provided in a hollow portion of the cylindrical unit and including an optical system configured to collect light from an object to be observed and form an image, and an imaging element configured to photoelectrically convert light collected by the optical system and output an imaging signal; a support unit including at least one set composed of two arm units and a joint unit linking one of the two arm units to the other in a rotationally movable manner and supporting, at its tip portion, the cylindrical unit and the imaging unit in a rotationally movable manner around an axis in a height direction of the cylindrical unit; and an arm manipulation unit provided on a side surface of the cylindrical unit corresponding to an upper side of an image based on the imaging signal and configured to accept a manipulation input that permits a rotational movement of the arm unit.

In the medical observation apparatus according to the present invention, in the above invention, the optical system may be capable of altering a magnification of an image of the object to be observed, and a magnification alteration input unit provided side by side with the arm manipulation unit along a height direction of the cylindrical unit and configured to accept an input that alters the magnification may be further included.

In the medical observation apparatus according to the present invention, in the above invention, the optical system may be capable of altering a focal distance to the object to be observed, and a focal distance alteration input unit provided side by side with the arm manipulation unit along a height direction of the cylindrical unit and configured to accept an input that alters the focal distance may be further included.

In the medical observation apparatus according to the present invention, in the above invention, the optical system may be capable of altering a magnification of an image of the object to be observed and a focal distance to the object to be observed, and an alteration input unit provided side by side with the arm manipulation unit along a height direction of the cylindrical unit and configured to accept, via manipulations in directions orthogonal to each other, an input that alters each of the magnification and the focal distance may be further included.

The medical observation apparatus according to the present invention, in the above invention, may further include an anti-slipping unit provided at least in an area that is in a side surface corresponding to an upper side of an image based on the imaging signal and is located farther from the support unit than the arm manipulation unit is and configured to prevent an object coming into contact from an outside from slipping relative to the cylindrical unit.

The medical observation apparatus according to the present invention, in the above invention, may further include a protruding unit provided at least in an end portion of the cylindrical unit that is located farther from the support unit than the arm manipulation unit is and corresponds to an upper side of an image based on the imaging signal and protruding in a diameter direction of the cylindrical unit.

A medical observation system according to the present invention includes: the above medical observation apparatus; a control device configured to perform signal processing on the imaging signal outputted by the medical observation apparatus to create image data for display; and a display device configured to display an image corresponding to image data created by the control device.

Advantageous Effects of Invention

According to the present invention, the arm manipulation unit that accepts a manipulation input that permits the movement of the arm unit in order to move the position of the imaging unit is provided on the side surface of the cylindrical unit, in the hollow portion of which the imaging unit is provided, that corresponds to the upper side of the image based on the imaging signal; hence, even when the user tilts the cylindrical unit to the side near to or far from the user in a state of grasping the cylindrical unit, the user can manipulate the arm manipulation unit using the index finger or the middle finger. Therefore, it is not necessary to provide another grip unit including an arm manipulation unit, and the cylindrical unit can be configured in a small size; thus, a medical observation apparatus and a medical observation system that can ensure the user's visual field and have good manipulability can be provided.

DESCRIPTION OF EMBODIMENT(S)

Figure 1:
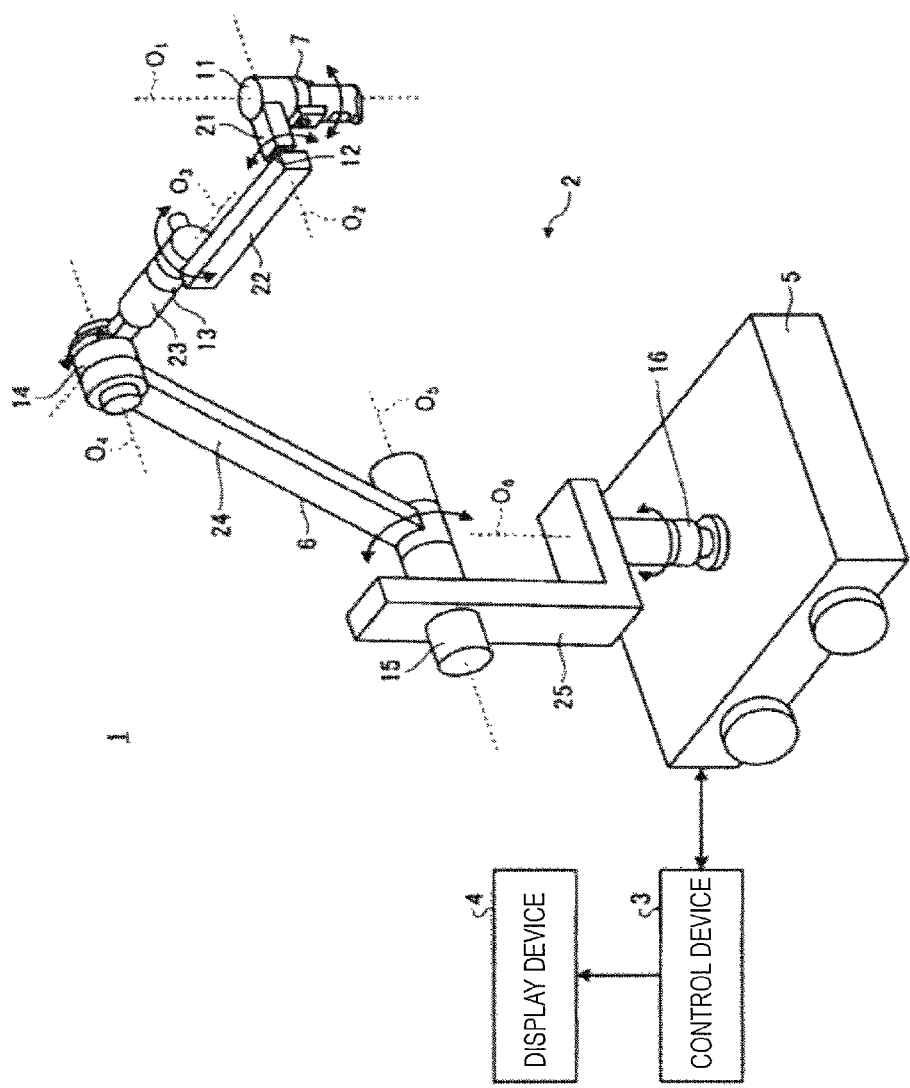
FIG. 1 is a perspective view showing an external configuration of a medical observation system according to Embodiment 1 of the present invention.

Hereinbelow, embodiments of the present invention (hereinafter, referred to as "embodiments") are described with reference to the appended drawings. The drawings are only schematic ones, and portions for which the relationships between dimensions and the proportions are different among drawings may be included in the drawings.

Embodiment 1

FIG. 1 is a diagram showing the configuration of a medical observation system according to Embodiment 1 of the present invention. A medical observation system 1 shown in the drawing includes a medical observation apparatus (hereinafter, referred to as an observation apparatus) 2 having a function as a microscope that images a minute structure of an object to be observed with magnification, a control device 3 that comprehensively controls the operation of the medical observation system 1, and a display device 4 that displays an image captured by the observation apparatus 2.

The observation apparatus 2 includes a base unit 5 capable of moving on the floor surface, a support unit 6 supported by the base unit 5, and a microscope unit 7 in a cylindrical shape that is provided at the tip of the support unit 6 and images a minute part of an object to be observed with magnification.

The support unit 6 includes a first joint unit 11, a first arm unit 21, a second joint unit 12, a second arm unit 22, a third joint unit 13, a third arm unit 23, a fourth joint unit 14, a fourth arm unit 24, a fifth joint unit 15, a fifth arm unit 25, and a sixth joint unit 16 in this order from the tip side to the root end side. The support unit 6 includes four sets each of which is composed of two arm units and a joint unit that links one of the two arm units (the tip side) to the other (the root end side) in a rotationally movable manner. Specifically, the four sets are (the first arm unit 21, the second joint unit 12, the second arm unit 22), (the second arm unit 22, the third joint unit 13, the third arm unit 23), (the third arm unit 23, the fourth joint unit 14, the fourth arm unit 24), and (the fourth arm unit 24, the fifth joint unit 15, the sixth arm unit 26).

The first joint unit 11 holds, on its tip side, the microscope unit 7 in a rotationally movable manner, and is held on its root end side in a state of being fixed to a tip portion of the first arm unit 21. The first joint unit 11 has a circular cylindrical shape, and holds the microscope unit 7 in a rotationally movable manner around a first axis $O_1$ that is the center axis in the height direction of the first joint unit 11. The first arm unit 21 has a shape extending from the side surface of the first joint unit 11 in a direction orthogonal to the first axis $O_1$.

The second joint unit 12 holds, on its tip side, the first arm unit 21 in a rotationally movable manner, and is held on its root end side in a state of being fixed to a tip portion of the second arm unit 22. The second joint unit 12 has a circular cylindrical shape, and holds the first arm unit 21 in a rotationally movable manner around a second axis $O_2$ that is the center axis in the height direction of the second joint unit 12 and is an axis orthogonal to the first axis $O_1$. The second arm unit 22 has a substantially L-shaped configuration, and is linked to the second joint unit 12 in an end portion of the longer line portion of the L shape.

The third joint unit 13 holds, on its tip side, the shorter line portion of the L shape of the second arm unit 22 in a rotationally movable manner, and is held on its root end side in a state of being fixed to a tip portion of the third arm unit 23. The third joint unit 13 has a circular cylindrical shape, and holds the second arm unit 22 in a rotationally movable manner around a third axis $O_3$ that is the center axis in the height direction of the third joint unit 13, is an axis orthogonal to the second axis $O_2$, and is parallel to the direction in which the second arm unit 22 extends. In the third arm unit 23, the tip side has a circular cylindrical shape, and a hole penetrating in a direction orthogonal to the height direction of the circular cylinder on the tip side is formed on the root end side.

The fourth joint unit 14 holds, on its tip side, the third arm unit 23 in a rotationally movable manner, and is held on its root end side in a state of being fixed to the fourth arm unit 24. The fourth joint unit 14 has a circular cylindrical shape, and holds the third arm unit 23 in a rotationally movable manner around a fourth axis $O_4$ that is the center axis in the height direction of the fourth joint unit 14 and is an axis orthogonal to the third axis $O_3$. In the fourth arm unit 24, a through-hole axially supported together with the fourth joint unit 14 is formed in a tip portion.

The fifth joint unit 15 holds, on its tip side, the fourth arm unit 24 in a rotationally movable manner, and is, on its root end side, attached fixedly to the fifth arm unit 25. The fifth joint unit 15 has a circular cylindrical shape, and holds the fourth arm unit 24 in a rotationally movable manner around a fifth axis $O_5$ that is the center axis in the height direction of the fifth joint unit 15 and is parallel to the fourth axis $O_4$. The fifth arm unit 25 is formed of an L-shaped portion and a bar-like portion extending downward from the horizontal line portion of the L shape. The fifth joint unit 15 is, on its root end side, attached to an end portion of the vertical line portion of the L shape of the fifth arm unit 25.

The sixth joint unit 16 holds, on its tip side, the fifth arm unit 25 in a rotationally movable manner, and is, on its root end side, attached fixedly to the upper surface of the base unit 5. The sixth joint unit 16 has a circular cylindrical shape, and holds the fifth arm unit 25 in a rotationally movable manner around an axis that is the center axis in the height direction of the sixth joint unit 16 and is orthogonal to the fifth axis $O_5$. A root end portion of the bar-like portion of the fifth arm unit 25 is attached to the tip side of the sixth joint unit 16.

The support unit 6 having such a configuration of the first axis $O_1$, the second axis $O_2$, the third axis $O_3$, the fourth axis $O_4$, the fifth axis $O_5$, and the sixth axis $O_6$ can achieve movements with 6 degrees of freedom of translation and rotation.

The first joint unit 11 to the sixth joint unit 16 include electromagnetic brakes that prohibit the rotational movements of the microscope unit 7 and the first arm unit 21 to the fifth arm unit 25, respectively. Each electromagnetic brake is released in a state where an arm manipulation switch 73 (described later) provided in the microscope unit 7 is pushed, and the rotational movements of the microscope unit 7 and the first arm unit 21 to the fifth arm unit 25 are permitted. An air brake may be used in place of the electromagnetic brake.

In the first joint unit 11 to the sixth joint unit 16, a hole through which a plurality of cables that transmit an imaging signal generated by an imaging unit 72 imaging an object to be observed and various signals for control transmitted by the control device 3 can be inserted is formed. Further, in the first arm unit 21 to the fifth arm unit 25, a hollow portion capable of housing a plurality of cables is formed. Therefore, cables are not exposed outside the observation apparatus 2, and persons and objects can be prevented from being caught in cables. In addition, the size can be made smaller than in the case of drawing a plurality of cables around outside the main body, and the user's visual field is not obstructed.

Figure 2:
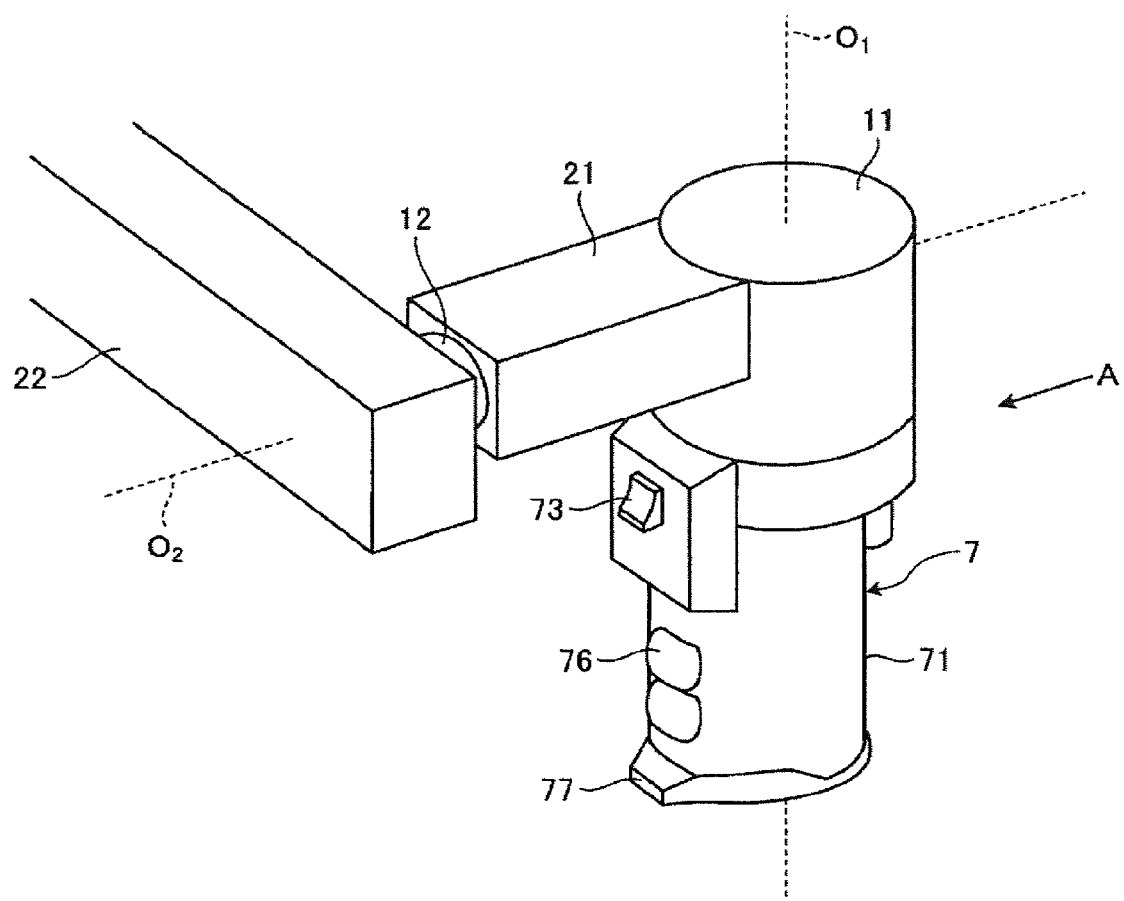
FIG. 2 is an enlarged perspective view showing the configuration of a microscope unit of a medical observation apparatus according to Embodiment 1 of the present invention and the vicinity thereof.
Figure 3:
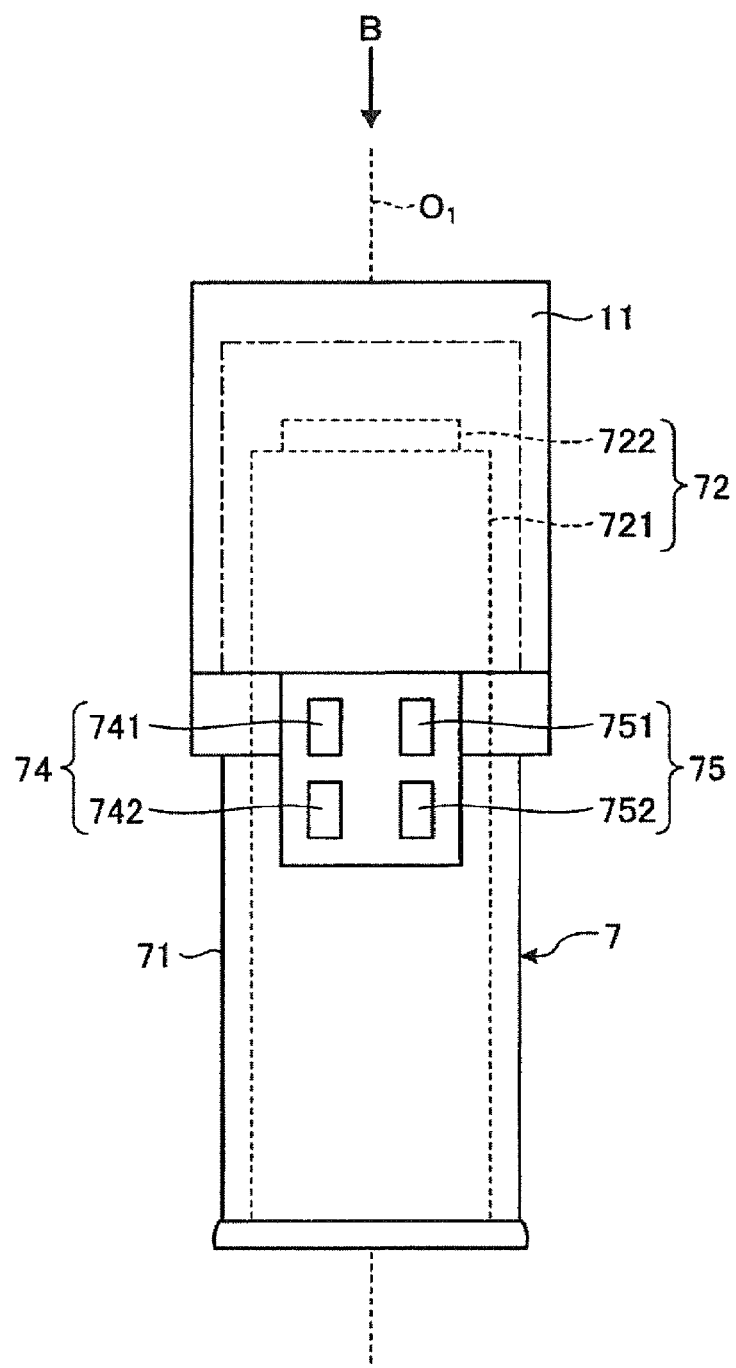
FIG. 3 is a side view as viewed in the direction of arrow A of FIG. 2.

FIG. 2 is an enlarged perspective view showing the configuration of the microscope unit 7 of the observation apparatus 2 and the vicinity thereof. FIG. 3 is a side view as viewed in the direction of arrow A of FIG. 2. The direction of arrow A is a direction orthogonal to the first axis $O_1$. The configuration of the microscope unit 7 will now be described with reference to FIG. 2 and FIG. 3.

The microscope unit 7 includes a cylindrical unit 71 having a circular cylindrical shape, an imaging unit 72 that is provided in the hollow portion of the cylindrical unit 71 and captures an image of an object to be observed with magnification, an arm manipulation switch (arm manipulation unit) 73 that accepts a manipulation input that releases the electromagnetic brakes in the first joint unit 11 to the sixth joint unit 16 to permit the rotational movements of the joint units, a magnification alteration switch 74 that accepts a manipulation input that alters the magnification in the imaging unit 72, a focal distance alteration switch 75 that accepts a manipulation input that alters the focal distance, which is the distance from the tip on the object to be observed side of an optical system 721 described later to the object to be observed, an anti-slipping unit 76 provided below the arm manipulation switch 73 and having an anti-slipping function, and a protruding unit 77 provided below the anti-slipping unit 76 at the edge of the lower end of the cylindrical unit 71 and protruding in the diameter direction of the cylindrical unit 71.

The cylindrical unit 71 has a circular cylindrical shape with a smaller diameter than the first joint unit 11, and a cover glass that protects the imaging unit 72 is provided on the opening surface at the lower end of the cylindrical unit 71 (not illustrated). The shape of the cylindrical unit 71 is not limited to a circular cylindrical shape, and may have a polygonal cylindrical shape.

The imaging unit 72 includes an optical system 721 that includes a plurality of lenses arranged such that their optical axes coincide with the first axis $O_1$ and that collects light from an object to be observed and forms an image, and an imaging element 722 that receives light collected by the optical system 721 and photoelectrically converts the light to generate an imaging signal.

The optical system 721 includes a plurality of lenses; and is capable of altering the magnification of the image of the object to be observed in accordance with the manipulation of the magnification alteration switch 74, and is capable of altering the focal distance to the object to be observed in accordance with the manipulation of the focal distance alteration switch 75.

Figure 4:
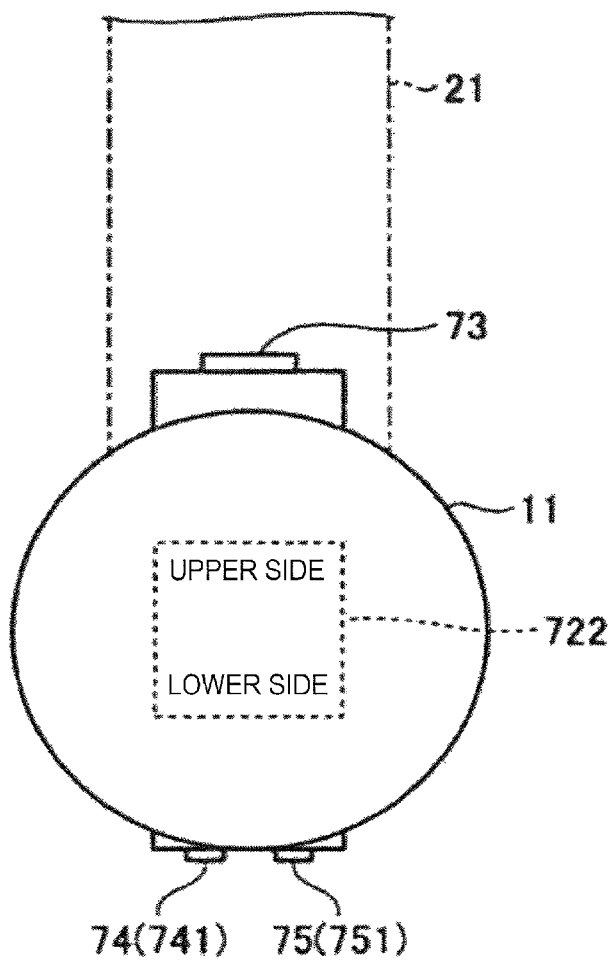
FIG. 4 is a top view as viewed in the direction of arrow B of FIG. 3 and is a schematic diagram as viewed excluding a first arm unit.

The imaging element 722 is formed using a charge-coupled device (CCD) or a complementary metal oxide semiconductor (CMOS). FIG. 4 is a top view as viewed in the direction of arrow B of FIG. 3 and is a top view as viewed excluding the first arm unit 21. As shown in FIG. 4, the imaging element 722 generates an imaging signal that gives an image in which the side where the arm manipulation switch 73 is provided is located on the upper side and the side where the magnification alteration switch 74 and the focal distance alteration switch 75 are provided is located on the lower side. The imaging signal outputted by the imaging element 722 is transmitted to the control device 3 via a transmission cable provided in the internal space of the support unit 6.

The imaging unit 72 has entered the interior of the first joint unit 11. In FIG. 3, the optical system 721 and the imaging element 722 installed in the hollow portion of the cylindrical unit 71 and the first joint unit 11 are schematically shown by the broken line. Further, in FIG. 3, a portion of the microscope unit 7 that has entered the interior of the first joint unit 11 and rotationally moves relative to the first joint unit 11 together with the cylindrical unit 71 is schematically shown by the alternate long and short dash line.

The arm manipulation switch 73 is a push-button switch. The electromagnetic brakes of the first joint unit 11 to the sixth joint unit 16 are released while the user keeps the arm manipulation switch 73 pushed. As described with reference to FIG. 4, the arm manipulation switch 73 is provided on the side surface of the cylindrical unit 71 corresponding to the upper side of the image based on the imaging signal generated by the imaging element 722. The user manipulates the microscope unit 7 while facing the side surface of the cylindrical unit 71 on which the magnification alteration switch 74 and the focal distance alteration switch 75 are provided. As is clear from FIG. 4, the side surface of the microscope unit 7 faced by the user is none other than the side surface corresponding to the lower side of the image based on the imaging signal generated by the imaging element 722. Therefore, the side surface on which the arm manipulation switch 73 is provided can also be said to be the side surface on the opposite side to the side surface faced by the user during the manipulation of the microscope unit 7 (see FIG. 3), or the side surface that is the user's blind spot during the manipulation of the microscope unit 7.

The magnification alteration switch 74 includes a zoom-in switch 741 that increases the magnification and a zoom-out switch 742 that decreases the magnification. The focal distance alteration switch 75 includes a long distance focus switch 751 that increases the focal distance to the object to be observed and a short distance focus switch 752 that decreases the focal distance to the object to be observed. The magnification alteration switch 74 and the focal distance alteration switch 75 are, as described above, provided on the side surface of the cylindrical unit 71 corresponding to the lower side of the image based on the imaging signal generated by the imaging element 722.

The anti-slipping unit 76 is provided in an area that is in the side surface corresponding to the upper side of the image based on the imaging signal generated by the imaging element 722 and is located farther from the support unit 6 than the arm manipulation switch 73 is, and prevents an object coming into contact from the outside (for example, the hand of the user) from slipping relative to the cylindrical unit 71. The anti-slipping unit 76 has two thin-thickness convexities aligned along the height direction of the cylindrical unit 71. The surface of the anti-slipping unit 76 is formed using a material that is hard for an object coming into contact from the outside to slip on. The shape of the anti-slipping unit 76 is not limited to that shown in FIG. 2, and may be any shape to the extent that it has the function of preventing the slipping of fingers of the user grasping the microscope unit 7.

The protruding unit 77 is provided in an end portion of the cylindrical unit 71 that is located farther from the support unit 6 than the arm manipulation switch 73 is and corresponds to the upper side of the image based on the imaging signal generated by the imaging element 722, and protrudes in the diameter direction of the cylindrical unit 71. The protruding unit 77 has the functions of preventing the visual field of the optical system 721 from being obstructed due to a finger of the user protruding downward from the lower end of the cylindrical unit 71 and preventing the cover lens from being made dirty due to a finger touching the cover lens.

Figure 5:
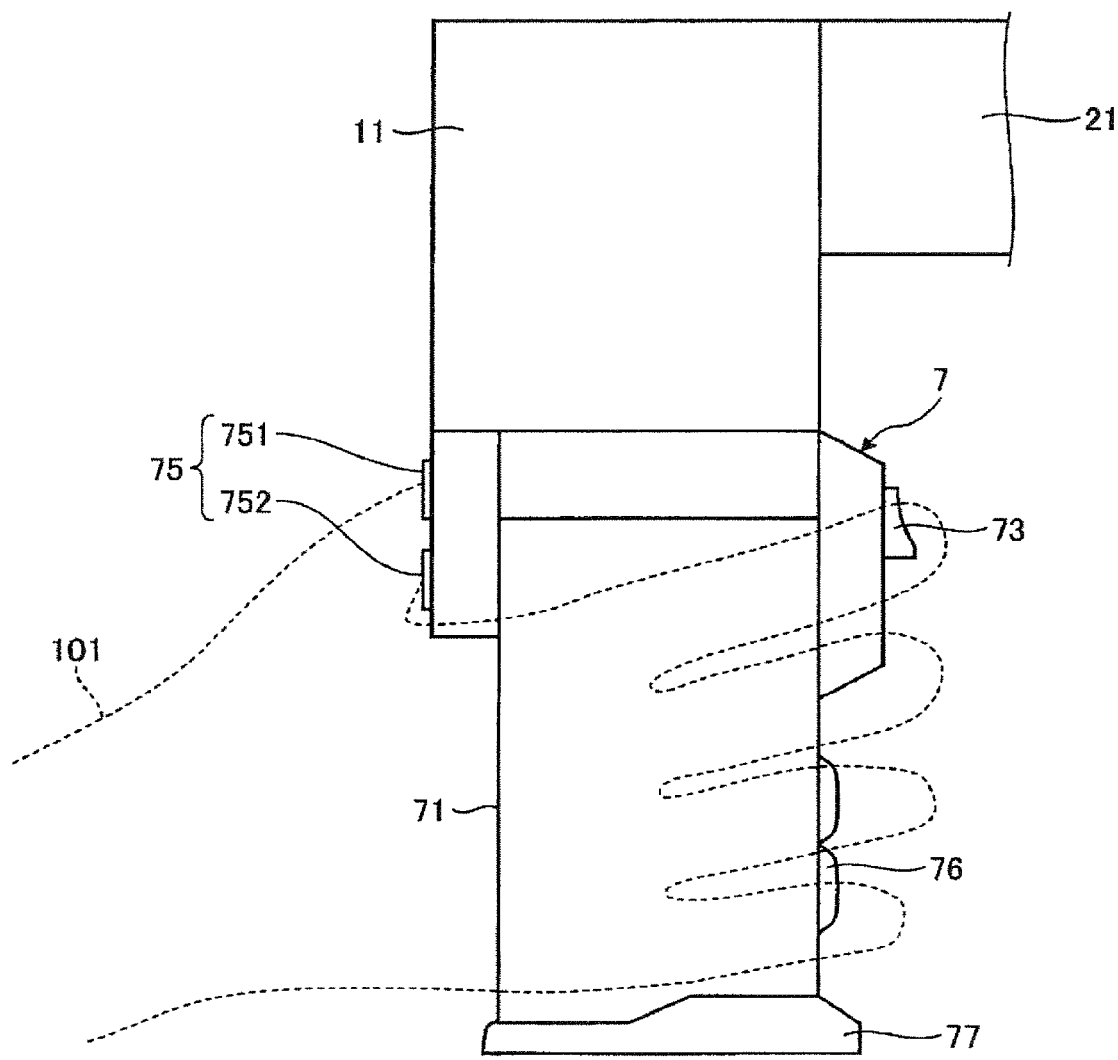
FIG. 5 is a diagram schematically showing a situation where a user manipulates the microscope unit of the medical observation apparatus according to Embodiment 1 of the present invention.

FIG. 5 is a diagram schematically showing a situation where the user manipulates the microscope unit 7. The user manipulates the microscope unit 7 while facing the side surface of the cylindrical unit 71 on which the magnification alteration switch 74 and the focal distance alteration switch 75 are provided. At this time, the user manipulates the support unit 6 while, in a state of grasping the microscope unit 7 with the right hand 101, keeping the arm manipulation switch 73 pushed with the index finger (or the middle finger or the ring finger). Thus, the user can manipulate the support unit 6 by pushing the arm manipulation switch 73 while naturally grasping the microscope unit 7.

In contrast, in the case of a conventional example in which, for example, the arm manipulation switch 73 exists on the thumb side (the same side as the focal distance alteration switch 75 of FIG. 5), when, in the drawing sheet of FIG. 5, the microscope unit 7 is tilted from the state shown in FIG. 5 to a state of down to the right or up to the right, the wrist bends gradually to lead to an unnatural posture, and it is difficult to continue pushing the arm manipulation switch. As is clear from the comparison with the conventional example, it can be said that the position of installation of the arm manipulation switch 73 in the Embodiment 1 is a suitable installation position in terms of improving the manipulability.

The control device 3 performs, in addition to the control of the medical observation system 1, a prescribed signal processing on an imaging signal received from the observation apparatus 2 to create image data for display. The control device 3 is configured using a central processing unit (CPU), a read-only memory (ROM), a random access memory (RAM), etc. The control device 3 may be installed in the base unit 5 and integrated with the observation apparatus 2.

The display device 4 receives image data for display created by the control device 3 from the control device 3, and displays an image corresponding to the image data. The display device 4 like this includes a liquid crystal display panel or an organic electro-luminescence (EL) display panel.

Figure 6:
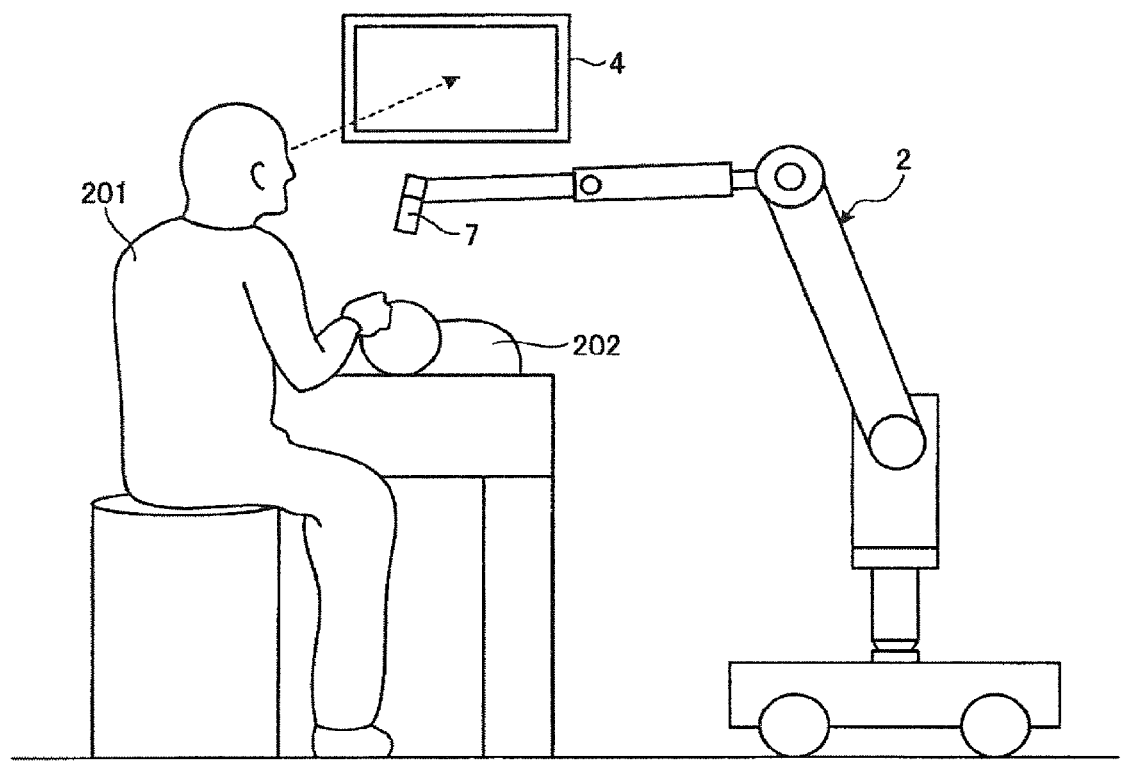
FIG. 6 is a diagram schematically showing a situation of an operation using the medical observation system according to Embodiment 1 of the present invention.

An overview of an operation performed using the medical observation system 1 having the above configuration will now be described. FIG. 6 is a diagram schematically showing a situation of an operation using the medical observation system 1. Specifically, FIG. 6 is a diagram schematically showing a situation in which an operator 201 performs an operation on the head of a patient 202 that is an object to be observed. The operator 201 who is the user, while visually observing an image displayed by the display device 4 (an image captured by the microscope unit 7), grasps the microscope unit 7 and moves it to a desired position in a state of keeping the arm manipulation switch 73 of the microscope unit 7 pushed, and adjusts the magnification and the focal distance to the object to be observed; thereby, determines the visual field. After determining the visual field of the microscope unit 7, the operator 201 removes the fingers from the arm manipulation switch 63. Thereby, the electromagnetic brake works in the first joint unit 11 to the sixth joint unit 16, and the visual field of the microscope unit 7 is fixed.

In order that the operator 201 can grasp the microscope unit 7 easily and the visual field at the time when the operator 201 views the display device 4 or the surgical site of the patient 202 may not be obstructed, it is preferable that, for example, the outer diameter of the cylindrical unit 71 be approximately 40 to 70 mm, and the height from the tip of the cylindrical unit 61 to the first joint unit 11 be approximately 80 to 200 mm. Further, it is preferable for the convexity of the anti-slipping unit 76 to have a thickness that does not impair the ease of grasping of the cylindrical unit 71 by the user (approximately several millimeters at most). Further, since the protrusion of the protruding unit 77 is highly likely to be sensed by the little finger, it is sufficient for the amount of protrusion to be approximately 0.5 to 2 cm.

In Embodiment 1 of the present invention described above, the arm manipulation switch 73 that accepts a manipulation input that permits the movements of the first arm unit 21 to the fifth arm unit 25 in order to move the position of the microscope unit 7 is provided on the side surface of the cylindrical unit 71, in the hollow portion of which at least part of the imaging unit 72 is provided, that corresponds to the upper side of the image based on the imaging signal; hence, even when the user tilts the microscope unit 7 to the side near to or far from the user in a state of grasping the microscope unit 7, the user can manipulate the arm manipulation switch 73 using the index finger or the middle finger. Therefore, it is not necessary to provide another grip unit including the arm manipulation switch 73, and the microscope unit 7 can be configured in a small size; thus, a medical observation apparatus and a medical observation system that can ensure the user's visual field and have good manipulability can be provided.

Furthermore, in the Embodiment 1, since the user grasps the periphery of the microscope unit 7 with the hand, the user can intuitively recognize the position of the optical axis of the optical system 721, that is, the direction of the imaging visual field, and can move the microscope unit 7 to a desired position easily. This is a very advantageous effect as compared to a case like a conventional operating microscope in which a grip provided with a switch for manipulation signal input is apart from the optical axis of the optical system and the optical axis direction cannot be intuitively recognized.

Furthermore, in the Embodiment 1, since the cylindrical unit 71 includes the anti-slipping unit 76 on its surface, the user can, when moving the microscope unit 7 in a state of grasping the cylindrical unit 71, cause the microscope unit 7 to reach a desired position without the hand slipping.

Furthermore, in the Embodiment 1, since the protruding unit 77 is provided at the lower end of the cylindrical unit 71, the cover glass can be prevented from being made dirty due to the user touching the cover glass provided at the lower end when the user grasps the cylindrical unit 71, and the optical path of illumination light etc. can be prevented from being obstructed; therefore, clear observed images can be acquired. In addition, the protruding unit 77 does not obstruct the visual field because the protruding unit 77 is formed in a position that is the user's blind spot during the manipulation and the operation.

Furthermore, in the Embodiment 1, the arm manipulation switch 73 is provided in a position that is the user's blind spot (the side surface on the opposite side to the side surface faced by the user); therefore, even when the user rotates or tilts the microscope unit 7 in a state of grasping the microscope unit 7 with the hand, the user can perform the manipulation of continuing pushing the arm manipulation switch 73 and the manipulation of pushing or releasing the arm manipulation switch 73 without a sense of incongruity.

Embodiment 2

A medical observation system according to Embodiment 2 of the present invention has a similar configuration to the medical observation system 1 described in Embodiment 1 except for the configuration of the imaging unit.

Figure 7:
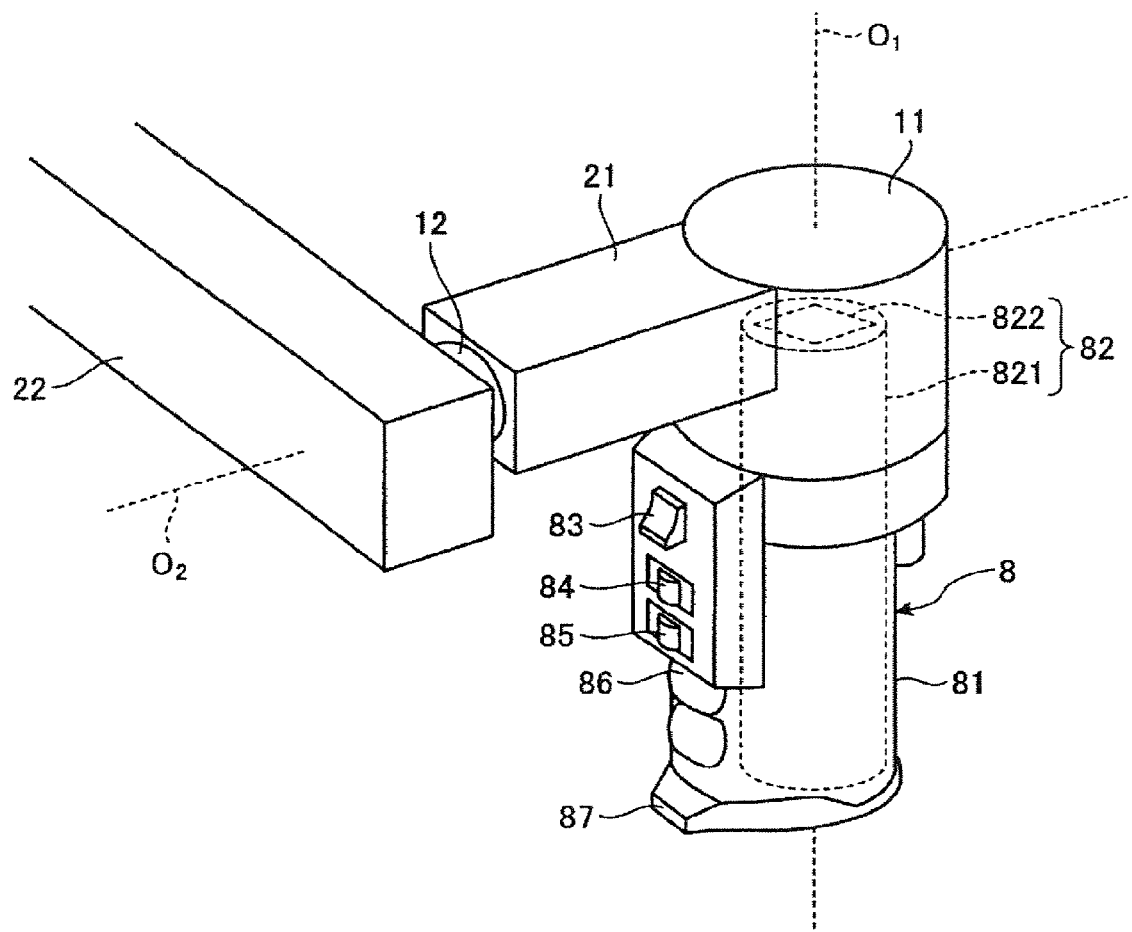
FIG. 7 is an enlarged perspective view showing the configuration of a microscope unit of a medical observation apparatus according to Embodiment 2 of the present invention and the vicinity thereof.

FIG. 7 is an enlarged perspective view showing the configuration of an imaging unit of an observation apparatus included in a medical observation system according to the Embodiment 2 and the vicinity thereof. A microscope unit 8 shown in the drawing includes a cylindrical unit 81 having a circular cylindrical shape, an imaging unit 82 that is provided in the cylindrical unit 81 and captures an image of an object to be observed with magnification, an arm manipulation switch (arm manipulation unit) 83 that is provided on the side surface of the cylindrical unit 81 and accepts a manipulation input that releases the electromagnetic brakes included in the first joint unit 11 to the sixth joint unit 16 to permit the rotational movements of the first arm unit 21 to the fifth arm unit 25, a magnification alteration lever (magnification alteration input unit) 84 that alters the magnification in the imaging unit 82, a focal distance alteration lever (focal distance alteration input unit) 85 that alters the focal distance, which is the distance from the tip on the object to be observed side of an optical system 821 described later in the imaging unit 82 to the object to be observed, an anti-slipping unit 86 provided below the arm manipulation switch 83 along the height direction of the cylindrical unit 81, and a protruding unit 87 provided below the anti-slipping unit 86 at the edge of the lower end of the cylindrical unit 81 and protruding in the diameter direction of the cylindrical unit 81.

The imaging unit 82 has a similar configuration to the imaging unit 72, that is, includes an optical system 821 and an imaging element 822. Also the arm manipulation switch 83 is a push-button switch similarly to the arm manipulation switch 73 described above. The arm manipulation switch 83 is provided on the side surface of the cylindrical unit 81 corresponding to the upper side in the image captured by the imaging element 822.

The magnification alteration lever 84 is a lever switch that is manipulable along the round direction orthogonal to the height direction of the cylindrical unit 81. The magnification alteration lever 84 is provided on the side surface of the cylindrical unit 81 below the arm manipulation switch 83 along the height direction of the cylindrical unit 81. For example, when the magnification alteration lever 84 is manipulated clockwise from the position shown in FIG. 7 along the round direction of the cylindrical unit 81, the magnification is increased; and when the magnification alteration lever 84 is manipulated counterclockwise along the round direction of the cylindrical unit 81, the magnification is decreased. The relationship between the direction of lever manipulation and the change in magnification may be opposite to the relationship described above.

The focal distance alteration lever 85 is, similarly to the magnification alteration lever 84, a lever switch that is manipulable along the round direction orthogonal to the height direction of the cylindrical unit 81. The focal distance alteration lever 85 is provided on the side surface of the cylindrical unit 81 below the magnification alteration lever 84 and above the anti-slipping unit 86 along the height direction of the cylindrical unit 81. For example, when the focal distance alteration lever 85 is manipulated clockwise from the position shown in FIG. 7 in the round direction of the cylindrical unit 81, the focal distance to the object to be observed is increased; and when the focal distance alteration lever 85 is manipulated counterclockwise along the round direction of the cylindrical unit 81, the focal distance to the object to be observed is decreased. The relationship between the direction of manipulation of the focal distance alteration lever 85 and the change in the focal distance to the object to be observed may be opposite to the relationship described above. Further, the vertical positional relationship between the magnification alteration lever 84 and the focal distance alteration lever 85 may be opposite.

By Embodiment 2 of the present invention described above, similar effects to Embodiment 1 can be obtained. In addition, in the Embodiment 2, since also the magnification alteration lever 84 and the focal distance alteration lever 85 are placed on the same side as the arm manipulation switch 83, the manipulability can be further improved.

The order of arrangement along the height direction of the cylindrical unit 81 of the arm manipulation switch 83, the magnification alteration lever 84, and the focal distance alteration lever 85 is not limited to that described above. For example, the arm manipulation switch 83 may be placed in the lowest position of the three switches, that is, nearest to the anti-slipping unit 86.

Embodiment 3

A medical observation system according to Embodiment 3 of the present invention has a similar configuration to the medical observation system 1 described in Embodiment 1 except for the configuration of the imaging unit.

Figure 8:
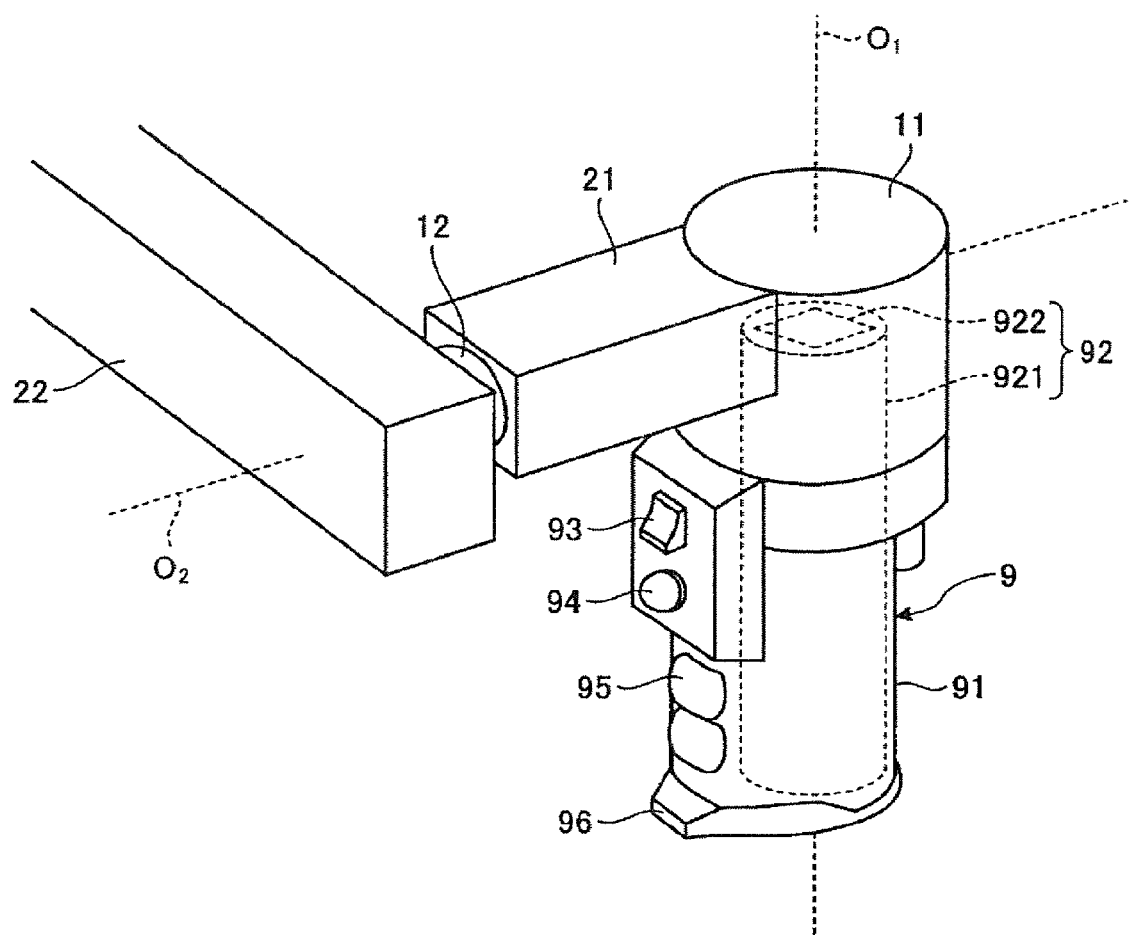
FIG. 8 is an enlarged perspective view showing the configuration of a microscope unit of a medical observation apparatus according to Embodiment 3 of the present invention and the vicinity thereof.

FIG. 8 is an enlarged perspective view showing the configuration of an imaging unit of an observation apparatus included in a medical observation system according to the Embodiment 3 and the vicinity thereof. A microscope unit 9 shown in the drawing includes a cylindrical unit 91 having a circular cylindrical shape, an imaging unit 92 that is provided in the cylindrical unit 91 and captures an image of an object to be observed with magnification, an arm manipulation switch 93 that is provided on the side surface of the cylindrical unit 91 and accepts a manipulation input that releases the electromagnetic brakes included in the first joint unit 11 to the sixth joint unit 16 to permit the rotational movements of the first arm unit 21 to the fifth arm unit 25, a cross lever (alteration input unit) 94 capable of altering the magnification and the focal distance to the object to be observed in the imaging unit 92, an anti-slipping unit 95 provided below the arm manipulation switch 83, and a protruding unit 96 provided below the anti-slipping unit 95 at the edge of the lower end of the cylindrical unit 91.

The imaging unit 92 has a similar configuration to the imaging unit 72, that is, includes an optical system 921 and an imaging element 922. Also the arm manipulation switch 93 is a push-button switch similarly to the arm manipulation switch 73 described above. The arm manipulation switch 93 is provided on the side surface of the cylindrical unit 91 corresponding to the upper side in the image captured by the imaging element 922.

The cross lever 94 is manipulable along the height direction of the cylindrical unit 91 and the round direction orthogonal to the height direction. The cross lever 94 is provided on the side surface of the cylindrical unit 91 below the arm manipulation switch 93 and above the anti-slipping unit 86 along the height direction of the cylindrical unit 91.

When the cross lever 94 is manipulated from the position shown in FIG. 8 along the height direction of the cylindrical unit 81, the magnification is altered; and when the cross lever 94 is manipulated from the position shown in FIG. 8 along the round direction of the cylindrical unit 81, the focal distance to the object to be observed is altered. For example, when the cross lever 94 is moved upward along the height direction of the cylindrical unit 81, the magnification is increased; and when the cross lever 94 is moved downward along the height direction of the cylindrical unit 81, the magnification is decreased. Further, when the cross lever 94 is moved clockwise along the round direction of the cylindrical unit 81, the focal distance to the object to be observed is increased; and when the cross lever 94 is moved counterclockwise along the round direction of the cylindrical unit 81, the focal distance to the object to be observed is decreased. The assignment of the direction of movement of the cross lever 94 and manipulation is not limited to that described herein.

By Embodiment 3 of the present invention described above, similar effects to Embodiment 1 described above can be obtained. In addition, in the Embodiment 3, since the magnification can be altered and the focal distance to the object to be observed can be altered by manipulating the cross lever 94 in a state where the cylindrical unit 81 is grasped, only little movement of fingers is needed even when the manipulations of altering the magnification and altering the focal distance to the object to be observed are repeated, and the possibility of causing wrong manipulation is significantly reduced. Further, in order to prevent a manipulation of the cross lever 94 toward between the height direction of the cylindrical unit 81 and the round direction of the cylindrical unit 81 (oblique pushing), the regulation with regard to the direction of oblique pushing may be made using a structure body; thereby, wrong manipulation can be lessened more.

Other Embodiments

Hereinabove, embodiments of the present invention are described; but the present invention is not limited to Embodiments 1 to 3 described above. For example, the area where the anti-slipping unit is provided may be further expanded in the round direction of the cylindrical unit, or the anti-slipping unit may be provided over the entire periphery. However, in this case, it is preferable that the anti-slipping unit not obstruct the user's visual field. As such an anti-slipping unit, for example, a trench may be formed on the surface of the cylindrical unit.

Further, the area of the lower edge end of the cylindrical unit in which the protruding unit is provided may be expanded as appropriate within the range in which the user's visual field at the time of using the medical observation apparatus is not obstructed. For example, the amount of protrusion of the portion entering the user's visual field may be set smaller than the amount of protrusion of the portion of the user's blind spot.

It is also possible to provide two imaging elements in the imaging unit to capture two images having a parallax and use the two images to create and display a three-dimensional image. In this case, the user may wear glasses for three-dimensional images, and can thereby visually observe a three-dimensional image displayed by the display device 4. When the display device 4 displays a three-dimensional image, the user can grasp the surgical site stereoscopically.

The support unit may include at least one set composed of two arm units and a joint unit that links one of the two arm units to the other in a rotationally movable manner.

Thus, the present invention may include various embodiments etc. without departing from the technical idea described in the claims.

REFERENCE SIGNS LIST 1 medical observation system
2 medical observation apparatus
3 control device
4 display device
5 base unit
6 support unit
7, 8, 9 microscope unit
11 first joint unit
12 second joint unit
13 third joint unit
14 fourth joint unit
15 fifth joint unit
16 sixth joint unit
21 first arm unit
22 second arm unit
23 third arm unit
24 fourth arm unit
25 fifth arm unit
71, 81, 91 cylindrical unit
72, 82, 92 imaging unit
73, 83, 93 arm manipulation switch
74 magnification alteration switch
75 focal distance alteration switch
76, 86, 95 anti-slipping unit
77, 87, 96 protruding unit
84 magnification alteration lever
85 focal distance alteration lever
94 cross lever
721, 821, 921 optical system
722, 822, 922 imaging element
741 zoom-in switch
742 zoom-out switch
751 long distance focus switch
752 short distance focus switch

The invention claimed is:

1. A medical observation apparatus comprising:
a body;
an imaging device provided in the body and including:
a lens barrel configured to collect light, and
an imager configured to photoelectrically convert the light collected by the lens barrel and output an imaging signal, the imager having an upper side and a lower side;
a support including at least one set composed of two arms and a joint unit linking one of the two arms to the other of the two arms in a rotationally movable manner and supporting, at a tip portion of the support, the body and the imager in a rotationally movable manner around an axis in a height direction of the body; and
an arm manipulation switch provided on a side surface of the body and configured to accept a manipulation input that permits a rotational movement of the two arms and the joint unit in a rotationally movable manner,
wherein the arm manipulation switch is located in an upper portion of the body in the height direction and at an operable position when the body is held by a user, and
wherein the arm manipulation switch is disposed on a side surface of the body that corresponds to the upper side of the imager that captures an image that is generated based on the imaging signal.

2. The medical observation apparatus according to claim 1,
wherein the lens barrel is configured to alter a magnification of an object to be captured by the imager, and
the medical observation apparatus further comprises a magnification alteration switch provided side by side with the arm manipulation switch along the height direction of the body and configured to accept an input that alters the magnification.

3. The medical observation apparatus according to claim 1,
wherein the lens barrel is configured to alter a focal distance to the object to be captured by the imager, and
the medical observation apparatus further comprises a focal distance alteration input switch provided side by side with the arm manipulation switch along the height direction of the body and configured to accept an input that alters the focal distance.

4. The medical observation apparatus according to claim 1,
wherein the lens barrel is configured to alter a magnification of an object to be captured by the imager and a focal distance to the object to be captured by the imager, and
the medical observation apparatus further comprises an alteration input switch provided side by side with the arm manipulation switch along the height direction of the body and configured to accept, via manipulations in directions orthogonal to each other, an input that alters each of the magnification and the focal distance.

5. The medical observation apparatus according to claim 1, further comprising an anti-slipping surface provided at least in an area that is in a side surface corresponding to a side of the imager that captures an upper side of an image that is generated based on the imaging signal and is located farther from the support than the arm manipulation switch is and configured to prevent an object that contacts the body from slipping relative to the body.

6. The medical observation apparatus according to claim 1, further comprising a protrusion provided at least in an end portion of the body that is located farther from the support than the arm manipulation switch is and corresponds to a side of the imager that captures an upper side of an image that is generated based on the imaging signal, the protrusion protruding in a diameter direction of the body.

7. A medical observation system comprising:
a medical observation apparatus, including:
a body,
an imaging device provided in the body and including:
a lens barrel configured to collect light, and
an imager configured to photoelectrically convert the light collected by the lens barrel and output an imaging signal, the imager having an upper side and a lower side,
a support including at least one set composed of two arms and a joint unit linking one of the two arms to the other of the two arms in a rotationally movable manner and supporting, at a tip portion of the support, the body and the imager in a rotationally movable manner around an axis in a height direction of the body, and
an arm manipulation switch provided on a side surface of the body and configured to accept a manipulation input that permits a rotational movement of the two arms and the joint unit in a rotationally movable manner;

control circuitry configured to perform signal processing on the imaging signal outputted by the medical observation apparatus to create image data for display; and a display configured to display an image corresponding to the image data created by the control circuitry, wherein the arm manipulation switch is located in an upper portion of the body in the height direction and at an operable position when the body is held by a user, and wherein the arm manipulation switch is disposed on a side surface of the body that corresponds to the upper side of the imager that captures an image that is generated based on the imaging signal.

8. The medical observation apparatus according to claim 1, wherein the support supports one end of the body and the lens barrel collects light from the other end of the body.

9. The medical observation system according to claim 7, wherein the support supports one end of the body and the lens barrel collects light from the other end of the body.

10. The medical observation apparatus according to claim 1, further comprising:

an anti-slipping surface provided on the side surface of the body and aligned with the arm manipulation switch in the height direction.

11. The medical observation system according to claim 7, further comprising:

an anti-slipping surface provided on the side surface of the body and aligned with the arm manipulation switch in the height direction.

12. The medical observation apparatus according to claim 1, wherein the body is cylindrical.

13. The medical observation apparatus according to claim 1, wherein the imaging device is provided in a hollow portion of the body.

14. The medical observation system according to claim 7, wherein the body is cylindrical.

15. The medical observation system according to claim 7, wherein the imaging device is provided in a hollow portion of the body.

16. The medical observation apparatus according to claim 3, wherein:

the focal distance alternation input switch corresponds to the lower side of the imager.

17. The medical observation apparatus according to claim 4, wherein:

the alteration input switch corresponds to the lower side of the imager.

18. The medical observation apparatus according to claim 1, wherein:

the arm manipulation switch is disposed on the side surface of the body that corresponds to the upper side of the imager that captures an upper side of the image that is generated based on the imaging signal.

19. The medical observation apparatus according to claim 7, wherein:

the arm manipulation switch is disposed on the side surface of the body that corresponds to the upper side of the imager that captures an upper side of the image that is generated based on the imaging signal.

* * * * *